United States Patent
Kahlert et al.

(10) Patent No.: US 10,344,254 B2
(45) Date of Patent: Jul. 9, 2019

(54) REACTOR PLANT AND PROCESS FOR CULTURING PHOTOTROPIC MICROORGANISMS

(75) Inventors: Wolfgang Kahlert, Körle (DE); Bernd-Ulrich Wilhelm, Petershagen (DE); Wolf-Dietrich Linke, Homberg/Efze (DE)

(73) Assignee: Sartorius AG, Gottingen (DE)

( * ) Notice: Subject to any disclaimer, the term of this patent is extended or adjusted under 35 U.S.C. 154(b) by 774 days.

(21) Appl. No.: 11/714,351

(22) Filed: Mar. 6, 2007

(65) Prior Publication Data

US 2007/0231886 A1 Oct. 4, 2007

(30) Foreign Application Priority Data

Mar. 28, 2006 (DE) .................. 10 2006 014 648

(51) Int. Cl.
*C12M 3/00* (2006.01)
*C12M 1/12* (2006.01)
*C12M 1/00* (2006.01)
*C12M 1/06* (2006.01)
*C12M 1/26* (2006.01)

(52) U.S. Cl.
CPC ............ *C12M 23/06* (2013.01); *C12M 21/02* (2013.01); *C12M 23/44* (2013.01); *C12M 27/02* (2013.01); *C12M 31/02* (2013.01); *C12M 33/14* (2013.01); *C12M 41/06* (2013.01)

(58) Field of Classification Search
CPC .............................. C12M 23/06; C12M 41/06
USPC ....................................................... 435/243
See application file for complete search history.

(56) References Cited

U.S. PATENT DOCUMENTS

| 5,179,012 A | 1/1993 | Gudin et al. |
| 6,602,703 B2 | 8/2003 | Dutil |
| 2003/0228684 A1* | 12/2003 | Burbidge et al. .......... 435/292.1 |
| 2005/0064577 A1* | 3/2005 | Berzin .......................... 435/266 |

FOREIGN PATENT DOCUMENTS

| DE | 691 14 311 T2 | 11/1995 |
| DE | 103 15 750 A1 | 10/2004 |
| EP | 0 261 872 A2 | 3/1988 |
| JP | 01-291 783 A | 11/1989 |
| JP | 05-023 166 A | 2/1993 |

OTHER PUBLICATIONS

Watanabe et al. Biotechnology and Bioengineering, 1995, 47:261-269.*

* cited by examiner

*Primary Examiner* — Bin Shen
(74) *Attorney, Agent, or Firm* — Gerald E. Hespos; Michael J. Porco; Matthew T. Hespos

(57) ABSTRACT

Reactor plant and process for culturing phototropic microorganisms with a reactor vessel and a photosynthetic module, which are connected with one another in a circulation circuit by a pump and can be controlled via a control unit, where in the circulation circuit or in the reactor vessel, a homogenizer is provided, where a light-intensity control of the photosynthetic module is provided, and where a bypass of the circulation circuit or of the reactor vessel with a filter device which is arranged externally of the reactor vessel for separating off extracellular products during the fermentation is provided.

17 Claims, 3 Drawing Sheets

REACTOR PLANT AND PROCESS FOR CULTURING PHOTOTROPIC MICROORGANISMS

BACKGROUND OF THE INVENTION

Field of the Invention

The invention relates to a reactor plant for culturing phototropic microorganisms with a reactor vessel and a photosynthetic module with light-intensity control, which are connected with one another in a circulation circuit by a pump and are controllable via a control unit.

The invention furthermore relates to a process for culturing phototropic microorganisms in a culture medium, in which process the culture medium together with the microorganisms is pumped, by means of a pump, in a circulation circuit from a reactor vessel through a photosynthetic module, the delivery rate of the pump being regulatable as a function of at least one reference quantity.

Description of the Related Art

DE 296 07 285 U1 discloses a reactor plant for culturing phototropic microorganisms where a reactor vessel and a photosynthetic module are connected with one another in a circulation circuit via a pump. A culture medium with the phototropic microorganisms to be cultured is circulated via pipelines of the circulation circuit. The pump in this system is controllable via a control unit which is connected to sensors for measuring the temperature, pH values, the oxygen partial pressure and the optical density. A bypass conveys the culture medium to a separation segment arranged within the reactor vessel, by which segment the biomass can be separated off.

The disadvantage of the prior art known plant and the process which it entails is that the fermentation must be terminated when the media constituents, or the substrate, have been consumed and when the desired biomass concentration in the separation segment has been achieved.

Furthermore, EP 0 968 273 B1 discloses a plant for the production of phototropic organisms and cell cultures with exposure to light by photochemical and photocatalytic reactions and photoinducible processes, where a reactor vessel and a photosynthetic module which are connected with one another in a circulation circuit by a pump and are controllable via a control unit. At a certain dry-matter concentration in the culture medium, the biomass is harvested. To this end, the culture suspension is conveyed to a harvesting device with the aid of the system pump. The harvesting device consists of a harvesting container, a harvesting pump, a separator and a biomass container. The separator separates the biomass from the liquid medium, which can be recirculated into the reactor vessel.

Moreover, DE 198 14 253 C2 discloses a plant and a method for the production of biomass by means of photosynthesis. Again, a reactor vessel and a photosynthetic module are connected with one another in a circulation circuit by a pump. The culture medium together with the microorganisms is pumped, by the pump, from the reactor vessel into the photosynthetic module, which is designed as a plate module, and travels back into the reactor vessel via a return pipe and a scrubber. Upon reaching a certain dry-matter concentration, the culture medium, or the biomass, are conveyed to a harvesting device with the aid of the pump. Here, the harvesting device consists of an intermediate reservoir, a delivery pump and a centrifuge. The centrifuge separates the biomass from the liquid medium, which is conveyed back into the reactor. The resulting biomass is conveyed to a processing device.

Again, the fermentation must be ended here when the media constituents have been consumed and the desired biomass concentration has been reached.

The object of the present invention is therefore to improve the existing plants and to obtain a prolonged fermentation time, which leads to a higher space-time yield. Also, it is intended to make possible, or improve, the separating off of extracellular products.

SUMMARY OF THE INVENTION

This object is achieved in conjunction with a reactor plant for culturing phototropic microorganisms by providing, in the circulation circuit or in the reactor vessel, a homogenizer, by providing a light-intensity control of the photosynthetic module and by providing a bypass of the circulation circuit or of the reactor vessel with a filter device which is arranged externally of the reactor vessel for separating off extracellular products during the fermentation.

By using a homogenizer, the flow properties in the system can be improved, which promotes both growth and productivity. Clogging of the cell or product separation devices, i.e. of the filter device, can be reduced. Separating off extracellular products during the fermentation using a filter device in a bypass of the circulation circuit reduces an adverse effect of the formed product on growth and/or productivity.

In accordance with the preferred embodiment of the invention, the homogenizer is designed as a comminuter. Both growth and productivity can be increased as the result of smaller aggregates. Also, the "illuminated area" of the organisms is greater for smaller aggregates than for larger aggregates. Simultaneously, clogging of the product separation device, and/or of the filter device for separating off extracellular products, is less pronounced for smaller aggregates. A defined membrane damage for obtaining intracellular products from a specific growth phase can be achieved as the result of the homogenizer or comminuter.

In accordance with a further preferred embodiment of the invention, the light intensity is controlled via the number of illumination means and/or by a dimmer function. Illumination means with at least two different wavelengths can be arranged in the photosynthetic module. As a result, the light can be regulated as a function of the concentration of the culture medium, in particular in conjunction with an optical density measurement.

In accordance with a further preferred embodiment of the invention, the photosynthetic module is equipped with a helically wound, transparent tube which is integrated into the circulation circuit. The use of a helically wound tube avoids, firstly, a multiplicity of connecting sites and, secondly, provides a relatively large illuminated area, which is achieved in a simple and inexpensive manner. For the illumination, a plurality of illumination means are arranged within the internal space surrounded by the helical tube. Also, a plurality of illumination means can be arranged concentrically around the helical tube, i.e. in parallel with the illumination means arranged in the internal space, on the outside of the tube. This allows an optimal light-intensity control to be achieved.

In accordance with a further preferred embodiment of the invention, baffles for generating a turbulent flow are arranged within the photosynthetic module. A turbulent flow is also promoted by high flow rates.

The advantage of a turbulent flow in the photosynthetic module is that the microorganisms are more frequently exposed to the light, whereby their growth is promoted.

In accordance with a further preferred embodiment of the invention, the filter device for separating off extracellular products is equipped with a cross-flow filter, a hollow-fiber filter or a membrane-adsorber filter. As the result of such filters, which are arranged in a bypass, continuous "harvesting" during the fermentation is made possible. An adverse effect on growth and/or productivity by the formed product is simultaneously prevented.

In accordance with a further preferred embodiment of the invention, there is provided a bypass of the circulation circuit or of the reactor vessel, in which bypass biomass is separated off in a device which is equipped with a cross-flow filter, a hollow-fiber filter, a centrifuge, a membrane-adsorber filter or a spin filter. Here, biomass can be separated in a simple, inexpensive and continuous manner.

The known processes for culturing phototropic microorganisms have the above-mentioned disadvantages.

A further object of the invention is therefore to improve the known processes and to make them more efficient.

This object is solved in a process for culturing phototropic microorganisms in a culture medium by homogenizing the culture medium in a homogenizer by comminution of its cell aggregates and by separating off extracellular products during the fermentation for harvesting purposes, via cross-flow or hollow-fiber or membrane-adsorber filters arranged in a bypass of the circulation circuit.

As the result of the comminution of the cell aggregates, both growth and productivity are increased. Moreover, clogging of the product separation devices and/or the filters employed for these purposes is less pronounced for smaller aggregates. By separating off the extracellular products via filters, a simple and inexpensive separation during the fermentation can be achieved in a continuous operation.

In accordance with a further preferred embodiment of the invention, and to obtain intracellular products from a certain growth phase, a specific damaging to the cells' membrane is accomplished by the comminution in the homogenizer, as the result of which intracellular products can be liberated and separated.

In accordance with a further preferred embodiment of the invention, biomass is separated off via cross-flow, hollow-fiber, membrane-adsorber or spin filters arranged in a bypass of the circulation circuit. It is also possible to centrifuge, and separate off, biomass in a centrifuge arranged in a bypass of the circulation circuit.

The biomass which has been separated off can be removed from the circulation circuit and conveyed to further processing. However, it is also possible to recirculate the biomass which has been separated off with addition of fresh medium to the circulation circuit.

All of the above-mentioned bypasses can be sterilized and are provided with the required means, such as pipes, connections, valves.

Further details of the invention can be seen from the detailed description which follows and the appended drawings, in which preferred embodiments of the invention are illustrated by way of example.

DETAILED DESCRIPTION OF THE PREFERRED EMBODIMENTS

Figure 1:
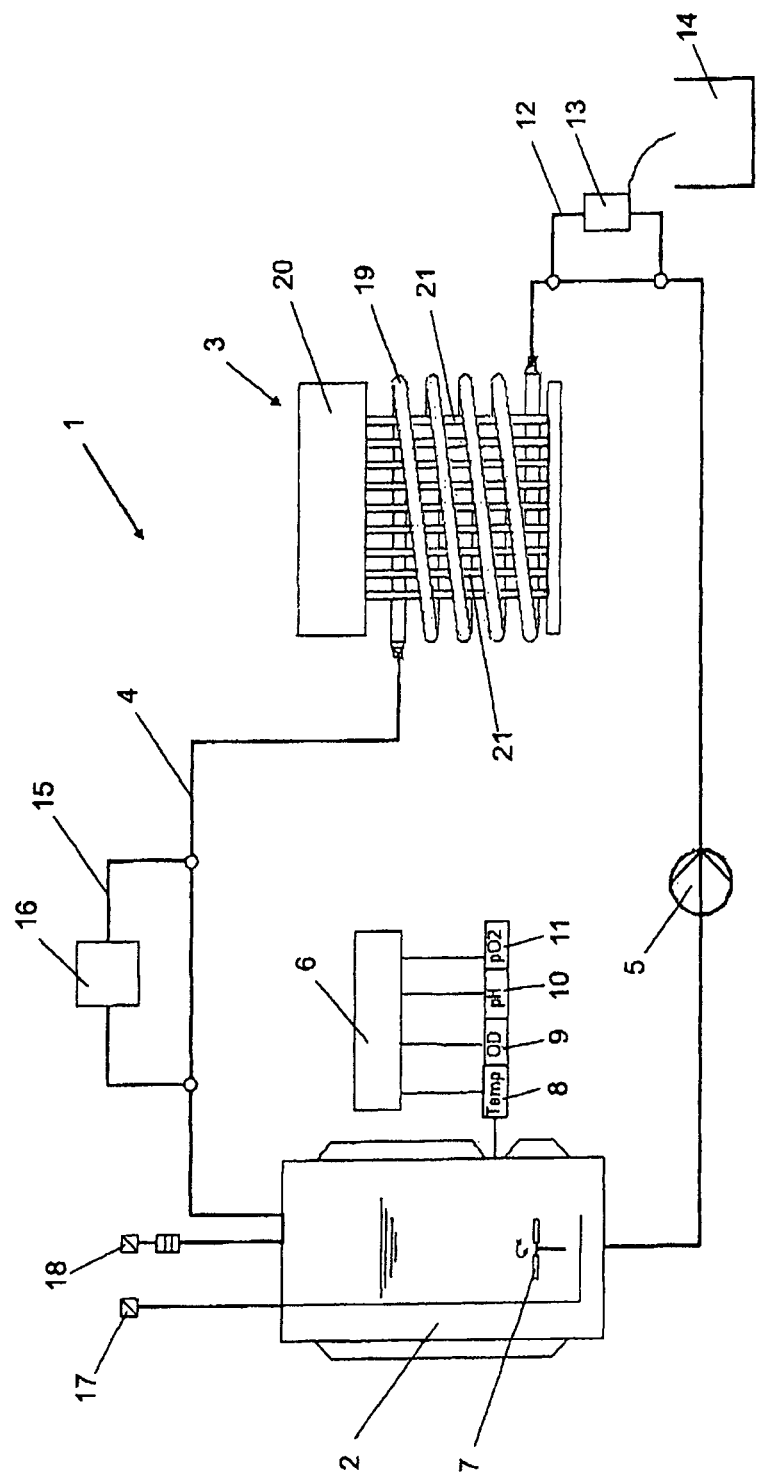
FIG. 1 is a diagrammatic representation of a reactor plant with a bypass which contains a filter for separating off product and which is arranged upstream of the photosynthetic module.

A reactor plant 1 for culturing phototropic microorganisms consists essentially of a reactor vessel 2, a photosynthetic module 3, a circulation circuit 4, a pump 5 and a control unit 6.

Within the reactor vessel 2, there is arranged a homogenizer 7 which is designed as a comminuter or mixer. The homogenizer 7 may also be arranged in the circulation circuit 4 or in a bypass of the reactor vessel 2, where the bypass is capable of being sterilized.

To measure the parameters of the culture medium arranged within the reactor vessel 2 and which has been inoculated with phototropic microorganisms, there is provided a temperature sensor 8, an OD sensor 9 for measuring the optical density, a pH sensor 10 for measuring the pH and a $pO_2$ sensor 11 for measuring the oxygen partial pressure, the data of which sensors being supplied to the control unit 6 which, in turn, controls the pump 5 and the illumination of the photosynthetic module 3.

A first bypass 12 is arranged between the pump 5 and the photosynthetic module 3 in the circulation circuit 4 and is equipped with a filter device 13 for separating off extracellular products during the fermentation. The product which has been separated off by the filter device 13 is recirculated to a collecting tank 14. A second bypass 15 is arranged for example in the return pipe of the circulation circuit 4 and can be equipped with a device 16 for separating off biomass by means of cross-flow filter, hollow-fiber filter, centrifuge, membrane-adsorber filter or spin filter.

The reactor vessel 2 is equipped in the known fashion with an air inlet 17 and a ventilation 18.

The photosynthetic module 3 is equipped with a helically wound, transparent tube 19 which is integrated into the circulation circuit 4. Within the internal space surrounded by the helical tube 19 there is arranged an illumination unit 20 which is provided with a multiplicity of illumination means 21. The light intensity of the illumination unit 20, or of the illumination means 21, is controlled by the control unit 6, for example via the optical density. The illumination intensity can be regulated both by the number of illumination means 21 which are switched on and via a dimmer function. Moreover, various illumination means 21 with different wavelengths can be employed. In this manner, it is also possible to simulate a photoperiod.

The tube 19 can be equipped with baffles (not shown) for generating a turbulent flow. Besides regulating the flow rate, this serves for preventing the formation of aggregates and adhering growth and for ensuring the desired metabolism.

The speed and/or delivery rate of the pump 5 is regulatable. For this purpose, the pump 5 can be regulated as a function of the biomass concentration, the adherence behavior of the biomass on the glass or on the required light which impinges per unit time. In the use example, the reference quantity for the pump regulation is the initial signal of the OD sensor 9 for measuring the optical density, which is a function of the biomass concentration. The filter device 13 for separating off extracellular products is equipped with a cross-flow filter. However, hollow-fiber filters or membrane-adsorber filters are also suitable. The device for separating off biomass 16 is also equipped with a cross-flow filter. Again, hollow-fiber filters, membrane-adsorber filters or spin filters are suitable. It is also possible to separate the biomass off with the aid of a centrifuge.

Figure 2:
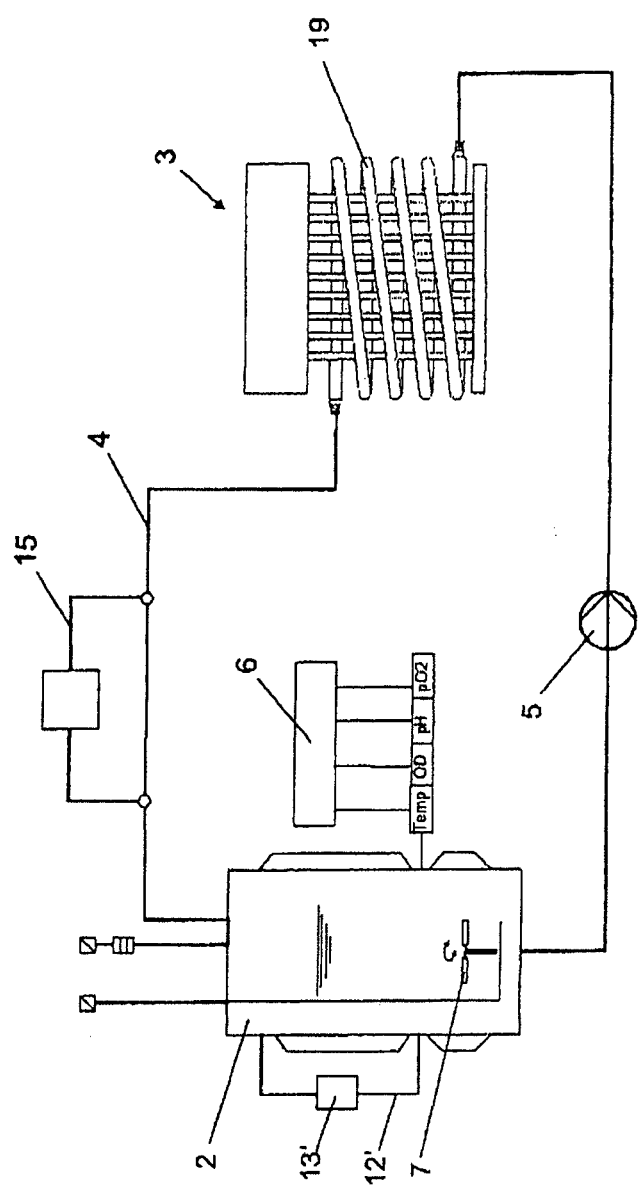
FIG. 2 is a diagrammatic representation of a reactor plant with a bypass which contains a filter, arranged outside the vessel, for separating off product and which is arranged upstream of the photosynthetic module.

As shown in FIG. 2, the first bypass 12', with its filter device 13', can also be connected in parallel with the reactor vessel 2. A collection tank for the product is not shown in FIG. 2.

Figure 3:
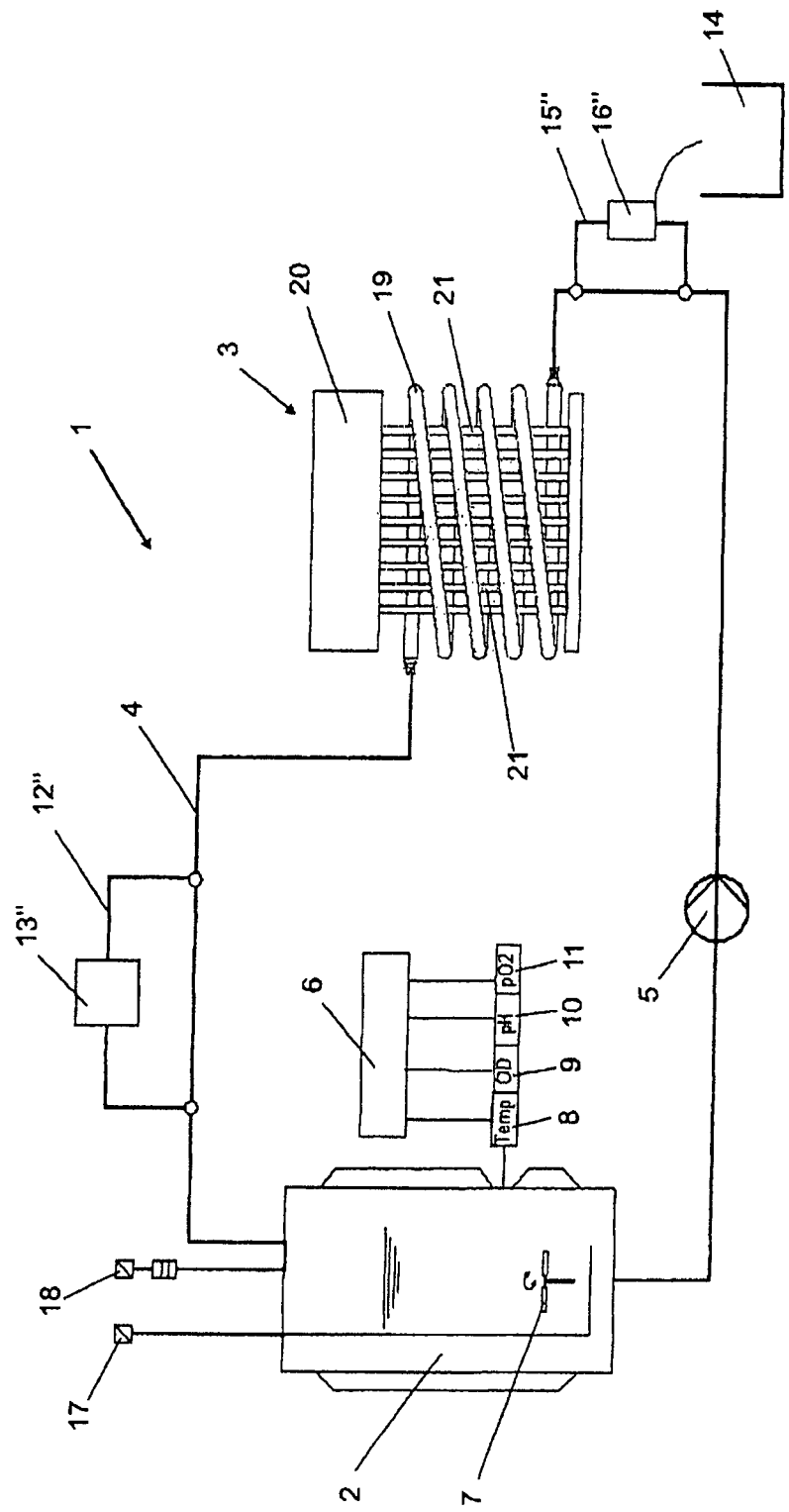
FIG. 3 is a diagrammatic representation of a reactor plant with a bypass which contains a filter for separating off biomass and which is arranged upstream of the photosynthetic module.

FIG. 3 shows a second bypass 15" with a device 16" for separating off biomass, where the biomass is collected in a collection tank 14.

Following an in-situ sterilization of the complete reactor plant, the system is filled with sterile medium via the reactor vessel 2 and is inoculated with the desired microorganism (cyanobacteria, single-celled and multi-celled plant organisms in compliance with GMP).

The culture medium together with the microorganisms is pumped through the photosynthetic module 3 by means of the pump 5. The speed of the pump is regulated as a function of the optical density of the culture medium with the microorganisms, i.e. as a function of the biomass concentration. The culture medium is homogenized in the homogenizer 7 by comminution of its cell aggregates. The extracellular products, but also intracellular products, are separated off during the fermentation, for harvesting purposes, via the filter device 13, 13', which is arranged in a first bypass 12, 12'.

To obtain intracellular products from a specific growth phase, a directed damaging of the cells' membranes is accomplished in the homogenizer 7 so that even intracellular products can be separated off. The homogenizer 7 may also be arranged at another point (not shown) of the circulation circuit 4. It is also possible to connect the homogenizer 7 via a bypass.

What is claimed is:

1. A reactor plant (1) for culturing phototropic microorganisms in a culture medium, comprising: a reactor vessel (2) through which the culture medium is circulated and a photosynthetic module (3) with a helically wound transparent tube (19) that communicates with the reactor vessel (2) via a circulation circuit (4) that includes a pump (5), the photosynthetic module (3) further including an illumination unit (20) aligned parallel to an axis of the helically wound transparent tube (19); a control unit (6) controlling at least the reactor vessel (2) and light-intensity of the illumination unit (20) of the photosynthetic module (3), a comminuter (7) provided inside the reactor vessel (2) and an optical density sensor (9) having a portion provided inside the reactor vessel (2), the optical density sensor (9) being operative to measure optical density of the culture medium inside the reactor vessel (2) as a function of biomass concentration of the culture medium inside the reactor vessel (2), and a bypass (12, 12', 12") of the circulation circuit (4) or of the reactor vessel (2) being provided, the bypass (12, 12', 12") having a filter device (13, 13', 13") arranged externally of the reactor vessel for separating off extracellular products during the fermentation, the control unit (6) is connected to the photosynthetic module (3) and controls the light-intensity of the photosynthetic module (3) as a function of the biomass concentration of the culture medium as determined by the optical density of the culture medium in the reactor vessel (2) sensed by the optical density sensor (9).

2. The reactor plant of claim 1, wherein the illumination unit (20) includes a dimmer or switch for selectively controlling plural illumination sources (21) of the illumination unit (20).

3. The reactor plant of claim 1, wherein the illumination unit (20) has at least two illumination means that are independently operable for producing illumination with at least two different wavelengths.

4. The reactor plant of claim 1, wherein the illumination unit 20 is arranged within an internal space surrounded by the helical tube (19).

5. The reactor plant of claim 1, further comprising baffles arranged within the photosynthetic module (3) for generating a turbulent flow.

6. The reactor plant of claim 5, wherein the filter device (13, 13', 13") for separating off extracellular products is equipped with a cross-flow filter, a hollow-fiber filter or a membrane-adsorber filter.

7. The reactor plant of claim 1, further comprising a bypass (15, 15") of the circulation circuit (4) or of the reactor vessel (2) with a device (16, 16") for separating off biomass by means of cross-flow filter, hollow-fiber filter, centrifuge, membrane-adsorber filter or spin filter.

8. The reactor plant of claim 1, wherein the control unit (6) further is connected to the pump (5) and controls a speed of the pump (5) as a function of the optical density measured by the optical density sensor (9).

9. Process for culturing phototropic microorganisms in a culture medium using the reactor plant of claim 1, where the culture medium together with the microorganisms is pumped in a circulation circuit (4) from a reactor vessel (2) through a photosynthetic module (3) by means of a pump (5), the delivery rate of the pump (5) being regulatable as a function of at least one reference quantity, wherein the improvement comprises the steps wherein the culture medium is homogenized in a homogenizer (7) by comminution of its cell aggregates and in that extracellular products are separated off during the fermentation, for harvesting purposes, via cross-flow or hollow-fiber or membrane-adsorber filters arranged in a bypass (12, 12', 12") of the circulation circuit (4).

10. Process according to claim 9, characterized in that, to obtain intracellular products from a certain growth phase, a specific damaging to the cells' membrane is accomplished by the comminution in the homogenizer (7).

11. Process according to claim 10, characterized in that biomass is separated off via cross-flow, hollow-fiber, membrane-adsorber or spin filters arranged in a bypass (15, 15") of the circulation circuit (4).

12. Process according to claim 11, characterized in that the biomass which has been separated off is removed from the circulation circuit (4) and conveyed to further processing.

13. Process according to claim 11, characterized in that the biomass which has been separated off is recirculated with addition of fresh medium to the circulation circuit (4).

14. Process according to claim 10, characterized in that biomass is centrifuged, and separated off, in a centrifuge arranged in a bypass (15, 15") of the circulation circuit (4).

15. A reactor plant (1) for culturing phototropic microorganisms in a culture medium, comprising:
a reactor vessel (2) for containing the culture medium, the reactor vessel (2) including a comminuter (7) provided inside the reactor vessel (2) and an optical density sensor (9) having a portion provided inside the reactor vessel (2) for sensing an optical density of the culture medium in the reactor vessel (2) as a function of a biomass concentration of the culture medium inside the reactor vessel (2);

a photosynthetic module (3) having illumination unit (20) for producing intensity controlled illumination and a transparent tube (19) wound around the illumination unit (20);

a pump (5) in communication with the reactor vessel (2) and the photosynthetic module (3) for circulating the culture medium from the reactor vessel (2) to the photosynthetic module (3) and back to the reactor vessel (2); and a control unit (6) communicating with the optical density sensor (9) and with the photosynthetic module (3), and the control unit (6) controlling a speed of the pump (5) and the intensity of the illumination produced by the illumination unit (20) as a function of the biomass concentration of the culture medium inside the reactor vessel (2) sensed by the optical density sensor (9).

16. The reactor plant of claim 15, wherein the control unit (6) controls the intensity of the illumination unit (20) by a dimmer or switch.

17. The reactor plant of claim 16, wherein the illumination unit (20) has at least two illumination means that are independently operable for producing light with at least two different wavelengths.

\* \* \* \* \*

UNITED STATES PATENT AND TRADEMARK OFFICE
CERTIFICATE OF CORRECTION

PATENT NO. : 10,344,254 B2  
APPLICATION NO. : 11/714351  
DATED : July 9, 2019  
INVENTOR(S) : Kahlert et al.

Page 1 of 1

It is certified that error appears in the above-identified patent and that said Letters Patent is hereby corrected as shown below:

On the Title Page

Item (73), should read "Sartorius Stedim Biotech GmbH, Goetting" instead of "Sartorius AG, Gottingen."

Signed and Sealed this  
Sixteenth Day of February, 2021

Drew Hirshfeld  
*Performing the Functions and Duties of the*  
*Under Secretary of Commerce for Intellectual Property and*  
*Director of the United States Patent and Trademark Office*